(12) United States Patent
Costabello et al.

(10) Patent No.: US 10,262,079 B1
(45) Date of Patent: Apr. 16, 2019

(54) DETERMINING ANONYMIZED TEMPORAL ACTIVITY SIGNATURES OF INDIVIDUALS

(71) Applicant: Accenture Global Solutions Limited, Dublin (IE)

(72) Inventors: Luca Costabello, Kildare (IE); Christophe Dominique Marie Gueret, Dublin (IE); Freddy Lecue, Castleknock (IE); Jeremiah Hayes, Dublin (IE); Nicholas McCarthy, Dublin (IE)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/141,636

(22) Filed: Sep. 25, 2018

(51) Int. Cl.
*G06F 17/30* (2006.01)
*G06F 1/16* (2006.01)

(52) U.S. Cl.
CPC ........ *G06F 17/30958* (2013.01); *G06F 1/163* (2013.01)

(58) Field of Classification Search
CPC .................. G06F 17/30958; G06F 17/5072
See application file for complete search history.

(56) References Cited

U.S. PATENT DOCUMENTS

2017/0140285 A1* 5/2017 Dotan-Cohen ........ G06N 5/048
2018/0129946 A1* 5/2018 Ellis ........................ H04L 67/22

OTHER PUBLICATIONS

Cai, et al; A comprehensive Survey of Graph Embedding: Problems, Techniques and Applications; IEEE vol. XX, No. XX Sep. 2017 (Year: 2017).*

Nickel, et al; A Review of Relatinal Machine Learning for Knowledge Graphs; Sep. 28, 2015 (Year: 2015).*

* cited by examiner

*Primary Examiner* — Amanda L Willis
(74) *Attorney, Agent, or Firm* — Harrity & Harrity, LLP

(57) ABSTRACT

A device may receive individual information associated with individual activities of an individual, and may aggregate the individual information, based on a time period, to generate aggregated individual information. The device may identify patterns in the aggregated individual information, and may determine states for the patterns based on state information associated with activities capable of being performed by individuals. The device may generate a sequential knowledge graph based on modifying a knowledge graph with the states and adding a sequence of activities to the knowledge graph, and may determine embeddings for the individual activities based on the sequential knowledge graph. The device may determine anonymized activity signatures for the individual activities based on the embeddings, and may combine the anonymized activity signatures to generate a time-based anonymized activity signature for the individual, wherein the time-based anonymized activity signature providing information that may be utilized without divulging the individual information.

20 Claims, 14 Drawing Sheets

US 10,262,079 B1

DETERMINING ANONYMIZED TEMPORAL ACTIVITY SIGNATURES OF INDIVIDUALS

BACKGROUND

A knowledge graph or an ontology includes types, properties, and interrelationships between entities that exist in a domain of discourse. A knowledge graph compartmentalizes variables needed for some set of computations, and establishes relationships between the variables. The fields of artificial intelligence, systems engineering, software engineering, biomedical informatics, library science, enterprise bookmarking, and/or the like create knowledge graphs or ontologies to limit complexity and organize information. A knowledge density of a knowledge graph is an average number of attributes and binary relations issued from a given entity, and is measured in facts per entity.

SUMMARY

According to some implementations, a device may include one or more memories, and one or more processors to receive a knowledge graph that includes state information associated with activities capable of being performed by individuals, and receive individual information associated with individual activities of an individual, where the individual information may be based on sensor information received from one or more sensors associated with the individual. The one or more processors may aggregate and normalize the individual information, based on a time period, to generate normalized individual information, and may identify patterns in the normalized individual information. The one or more processors may associate activity annotations with the patterns based on the state information in the knowledge graph, where a plurality of the activity annotations may be associated to create a temporal sequence of activities, and may modify the knowledge graph with the activity annotations to generate a modified knowledge graph. The one or more processors may determine embeddings for the individual activities of the individual based on the modified knowledge graph, and may determine anonymized activity signatures for the individual activities of the individual based on the embeddings by determining a vector element based on the embeddings, determining a magnitude parameter of the vector element to create a plurality of intermediate activity signatures, each intermediate activity signature being associated with an activity in the temporal sequence of activities, and aggregating the plurality of intermediate activity signatures to create an overall anonymized activity signature for the temporal sequence of activities. The one or more processors may generate a time-based anonymized activity signature for the individual based on the anonymized activity signatures, and may utilize the time-based anonymized activity signature to perform an action.

According to some implementations, a non-transitory computer-readable medium may store instructions that include one or more instructions that, when executed by one or more processors, cause the one or more processors to monitor individual activities of an individual over a time period based on sensor information received from one or more sensors associated with the individual, and receive, over the time period, individual information associated with the individual activities of the individual based on monitoring the individual activities. The one or more instructions may cause the one or more processors to aggregate and normalize the individual information, based on the time period, to generate normalized aggregated individual information, and identify patterns in the normalized aggregated individual information. The one or more instructions may cause the one or more processors to associate states with the patterns based on state information associated with activities capable of being performed by individuals, and generate a sequential knowledge graph based on modifying a knowledge graph with the states and adding a sequence of activities to the knowledge graph. The one or more instructions may cause the one or more processors to determine embeddings for the individual activities of the individual based on the sequential knowledge graph, and determine anonymized activity signatures for the individual activities of the individual based on the embeddings. The one or more instructions may cause the one or more processors to generate a time-based anonymized activity signature for the individual based on the anonymized activity signatures, and utilize the time-based anonymized activity signature to perform an action.

According to some implementations, a method may include receiving, over a time period, individual information associated with individual activities of an individual, and aggregating the individual information, based on the time period, to generate aggregated individual information. The method may include identifying patterns in the aggregated individual information, and determining states for the patterns based on state information associated with activities capable of being performed by individuals. The method may include generating a sequential knowledge graph based on modifying a knowledge graph with the states and adding a sequence of activities to the knowledge graph, and determining embeddings for the individual activities of the individual based on the sequential knowledge graph. The method may include determining anonymized activity signatures for the individual activities of the individual based on the embeddings, and combining the anonymized activity signatures to generate a time-based anonymized activity signature for the individual, wherein the time-based anonymized activity signature may provide information that may be utilized without divulging the individual information.

DETAILED DESCRIPTION

The following detailed description of example implementations refers to the accompanying drawings. The same reference numbers in different drawings may identify the same or similar elements.

Wearable devices are smart electronic devices (e.g., electronic devices with micro-controllers) that can be incorporated into clothing or worn on the body as implants or accessories. Wearable devices, such as activity trackers, monitor and track fitness-related information, such as a distance walked, a calorie consumption, a heart rate, a quality of sleep, and/or the like. Such information may be utilized to compare fitness-related information associated with different individuals. However, such a comparison requires unnecessary disclosure of personal information associated with the different individuals.

Some implementations described herein provide an activity signature platform that determines anonymized temporal activity signatures of individuals. For example, the activity signature platform may receive, over a time period, individual information associated with individual activities of an individual, and may aggregate the individual information, based on the time period, to generate aggregated individual information. The activity signature platform may identify patterns in the aggregated individual information, and may determine states for the patterns based on state information associated with activities capable of being performed by individuals. The activity signature platform may generate a sequential knowledge graph based on modifying a knowledge graph with the states and adding a sequence of activities to the knowledge graph, and may determine embeddings for the individual activities of the individual based on the sequential knowledge graph. The activity signature platform may determine anonymized activity signatures for the individual activities of the individual based on the embeddings, and may combine the anonymized activity signatures to generate a time-based anonymized activity signature for the individual, wherein the time-based anonymized activity signature provides information that may be utilized without divulging the individual information.

In this way, the activity signature platform may provide anonymized activity signatures of individuals that may be compared without divulging personal information associated with the individuals. The activity signature platform may provide recommendations to the individuals regarding their activities, and thus, may aid in improving the quality of life of the individuals.

Figure 1A:
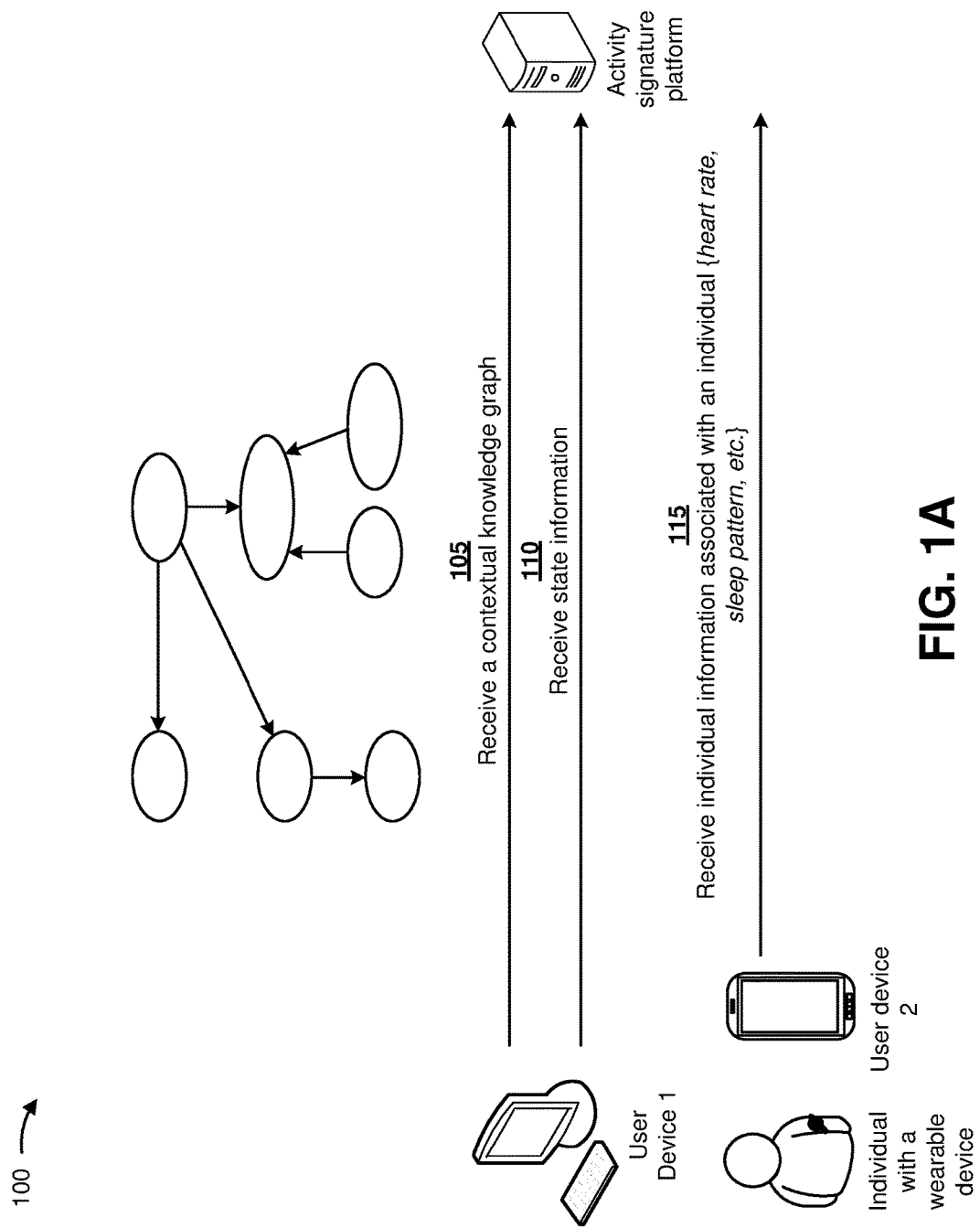
FIGS. 1A-1I are diagrams of an overview of an example implementation described herein.

FIGS. 1A-1I are diagrams of an overview of an example implementation 100 described herein. As shown in FIG. 1A, a first user device (e.g., user device 1) and a second user device (e.g., user device 2) may be associated with an activity signature platform, and the second user device may be associated with an individual with a wearable device (e.g., a smart watch, a pair of smart glasses, a heart rate monitor, a fitness tracker, etc.). As shown in FIG. 1A, and by reference number 105, a user of the first user device (e.g., via a user interface provided to the user) may cause the first user device to provide, to the activity signature platform, a contextual knowledge graph, and the activity signature platform may receive the contextual knowledge graph. In some implementations, the contextual knowledge graph may be associated with activities of individuals, such as, for example, running, walking, playing a sport, resting, sleeping, working at a desk, and/or the like.

As further shown in FIG. 1A, and by reference number 110, the user may cause the first user device to provide, to the activity signature platform, state information, and the activity signature platform may receive the state information. In some implementations, the state information may include information indicating activities of individuals such as, for example, riding a bike, hiking, traveling in a vehicle, running, walking, playing a sport, resting, sleeping, working at a desk, and/or the like.

As further shown in FIG. 1A, and by reference number 115, the wearable device may provide, to the activity signature platform, individual information, and the activity signature platform may receive the individual information from the wearable device. In some implementations, the individual may cause the second user device to receive the individual information from the wearable device, and the second user device may provide the individual information to the activity signature platform. In some implementations, the individual information may include information indicating activities of the individual (e.g., information indicating a heart rate of the individual, information indicating a sleep pattern of the individual, information indicating that the individual is riding a bike, hiking, traveling in a vehicle, running, walking, playing a sport, resting, sleeping, working at a desk, etc., and/or the like); and/or the like.

In some implementations, the contextual knowledge graph and/or the state information may not be stored in the first user device, but the first user device may cause the contextual knowledge graph and/or the state information to be provided from a resource, storing the contextual knowledge graph and/or the state information, to the activity signature platform. In some implementations, the contextual knowledge graph, the state information, and/or the individual information may be stored in the activity signature platform. In some implementations, although FIGS. 1A-1I relate to an individual activity domain, the activity signature platform may be used with any type of domain and may be domain agnostic.

Figure 1B:
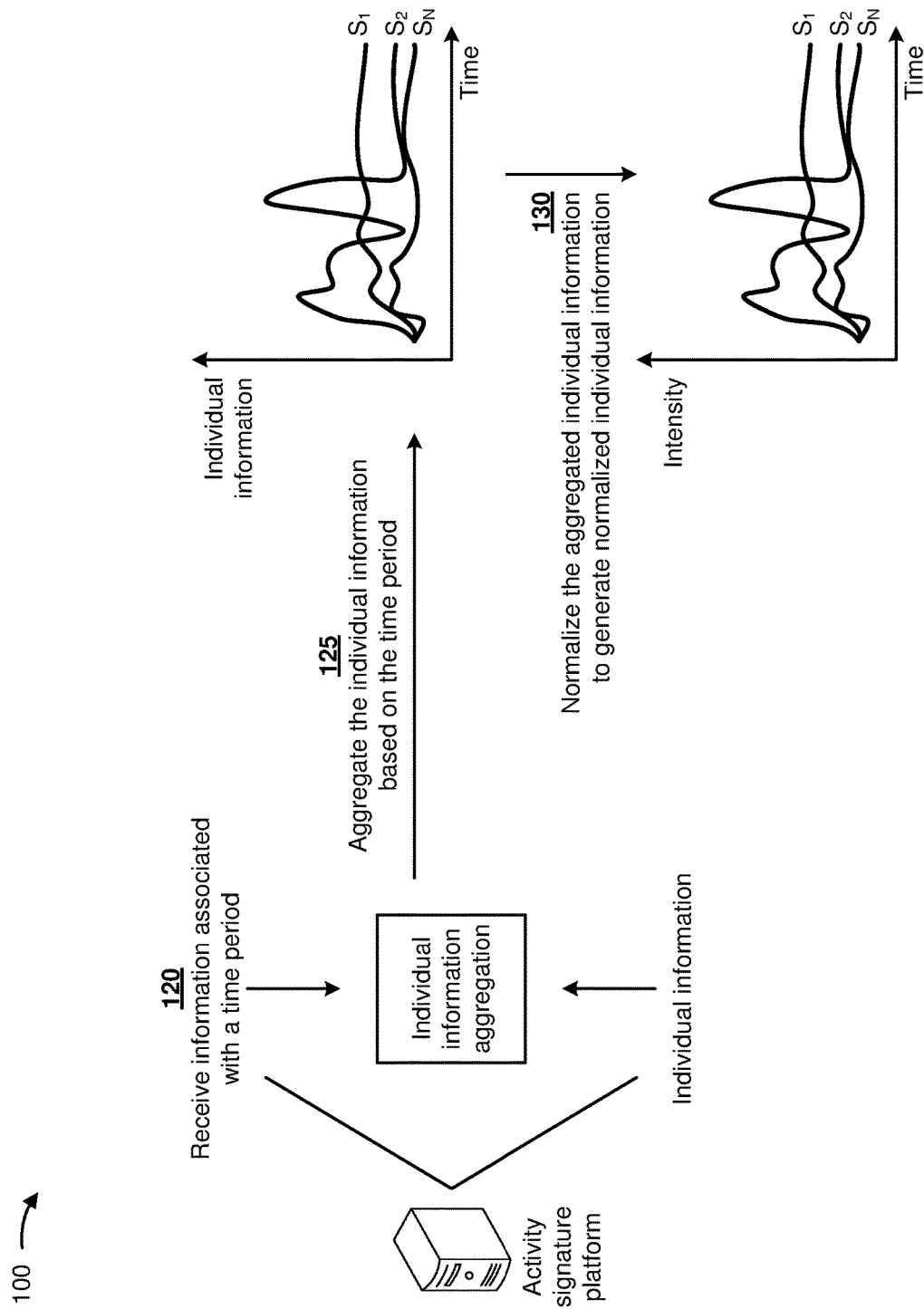

As shown in FIG. 1B, and by reference number 120, the activity signature platform may receive information associated with a time period (e.g., from the first user device and/or the second user device). In some implementations, the time period may include a range of minutes, hours, days, years, and/or the like. For example, the time period may include twenty-four hours (or one day), three-hundred and sixty-five days (or one year), and/or the like. In some implementations, the activity signature platform may collect the individual information over the time period.

As further shown in FIG. 1B, and by reference number 125, the activity signature platform may aggregate the individual information based on the time period. In some implementations, the activity signature platform may aggregate the information indicating the heart rate of the individual, from the individual information, to generate aggregated heart rate information (e.g., $S_1$) during the time period. In some implementations, the activity signature platform may aggregate the information indicating the sleep pattern of the individual, from the individual information, to generate aggregated sleep pattern information (e.g., $S_2$) during the time period. In some implementations, the activity signature platform may aggregate the information indicating the schedule of the individual, from the individual information, to generate aggregated schedule information (e.g., $S_3$) during the time period. In some implementations, the activity signature platform may aggregate all the individual information until a final portion of the individual information is aggregated (e.g., $S_N$) for the time period.

As further shown in FIG. 1B, and by reference number 130, the activity signature platform may normalize the aggregated individual information to generate normalized individual information. In some implementations, the activity signature platform may normalize the aggregated individual information by adjusting values measured on different scales (e.g., aggregated heart rate information, aggregated sleep pattern information, aggregated schedule information, and/or the like) to a notionally common scale (e.g., an intensity). In some implementations, the activity signature platform may utilize a Min-Max normalization technique, a Z-score normalization technique, a decimal scaling normalization technique, and/or the like to normalize the aggregated individual information and generate the normalized individual information.

Figure 1C:
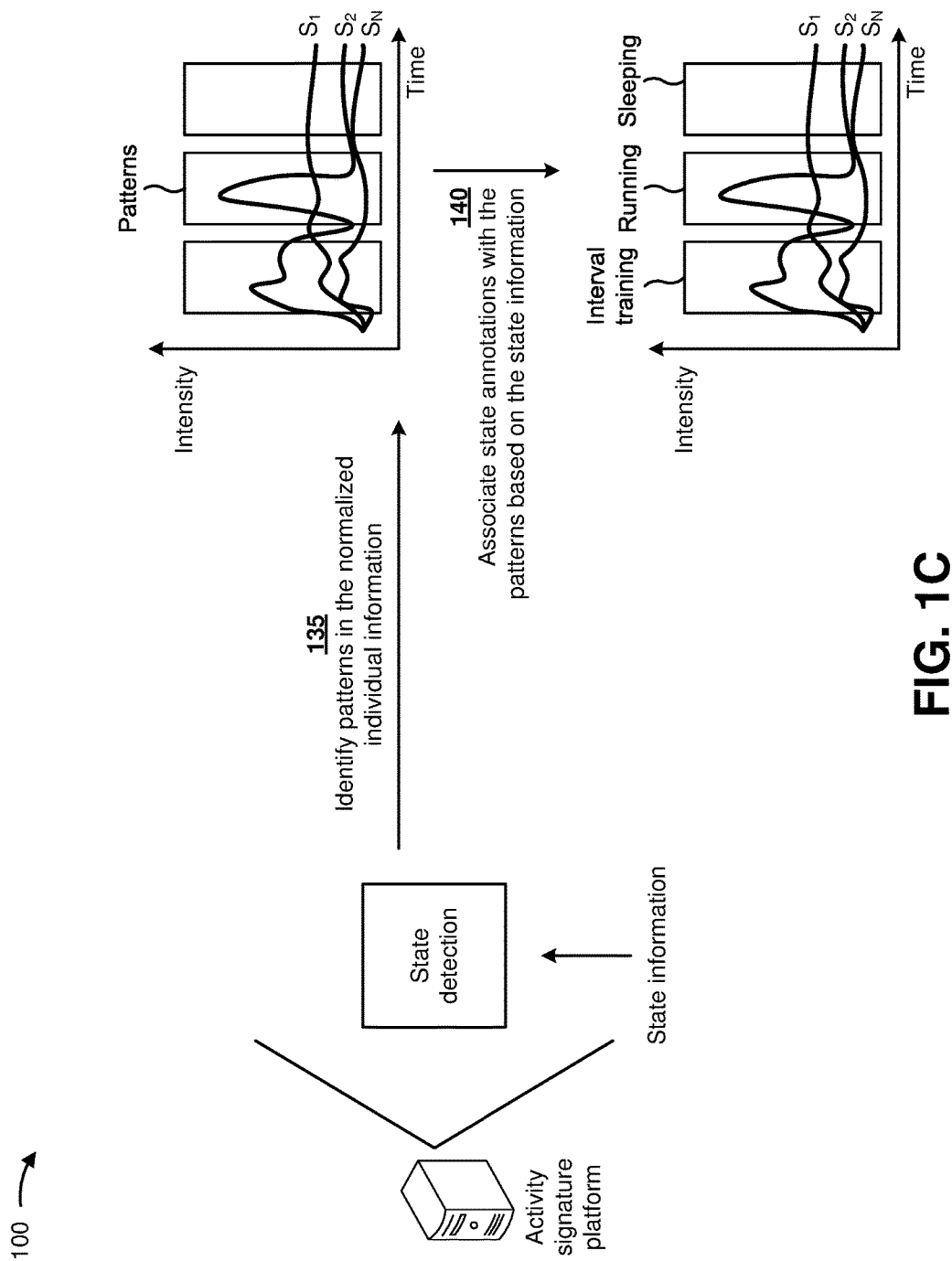

As shown in FIG. 1C, and by reference number 135, the activity signature platform may identify patterns in the normalized individual information. In some implementations, the activity signature platform may utilize a machine learning model (e.g., a pattern recognition model) to identify the patterns in the normalized individual information.

In some implementations, the activity signature platform may perform a training operation on the machine learning model with historical normalized individual information (e.g., historical information showing different activities of individuals, heart rates of the individuals for the different activities, sleep patterns of the individuals, schedules of the individuals for the different activities, and/or the like). For example, the activity signature platform may separate the historical normalized individual information into a training set, a validation set, a test set, and/or the like. In some implementations, the activity signature platform may train the machine learning model using, for example, an unsupervised training procedure and based on the training set of the historical normalized individual information. For example, the activity signature platform may perform dimensionality reduction to reduce the historical normalized individual information to a minimum feature set, thereby reducing resources (e.g., processing resources, memory resources, and/or the like) to train the machine learning model, and may apply a classification technique, to the minimum feature set.

In some implementations, the activity signature platform may use a logistic regression classification technique to determine a categorical outcome (e.g., that the historical normalized individual information includes patterns associated with the different activities). Additionally, or alternatively, the activity signature platform may use a naïve Bayesian classifier technique. In this case, the activity signature platform may perform binary recursive partitioning to split the historical normalized individual information into partitions and/or branches, and use the partitions and/or branches to perform predictions (e.g., that the historical normalized individual information includes patterns associated with the different activities). Based on using recursive partitioning, the activity signature platform may reduce utilization of computing resources relative to manual, linear sorting and analysis of data points, thereby enabling use of thousands, millions, or billions of data points to train the machine learning model, which may result in a more accurate model than using fewer data points.

Additionally, or alternatively, the activity signature platform may use a support vector machine (SVM) classifier technique to generate a non-linear boundary between data points in the training set. In this case, the non-linear boundary is used to classify test data into a particular class.

Additionally, or alternatively, the activity signature platform may train the machine learning model using a supervised training procedure that includes receiving input to the machine learning model from a subject matter expert, which may reduce an amount of time, an amount of processing resources, and/or the like to train the machine learning model of activity automatability relative to an unsupervised training procedure. In some implementations, the activity signature platform may use one or more other model training techniques, such as a neural network technique, a latent semantic indexing technique, and/or the like. For example, the activity signature platform may perform an artificial neural network processing technique (e.g., using a two-layer feedforward neural network architecture, a three-layer feedforward neural network architecture, and/or the like) to perform pattern recognition with regard to patterns of the historical normalized individual information that are associated with the different activities. In this case, using the artificial neural network processing technique may improve an accuracy of the trained machine learning model generated by the activity signature platform by being more robust to noisy, imprecise, or incomplete data, and by enabling the activity signature platform to detect patterns and/or trends undetectable to human analysts or systems using less complex techniques.

As further shown in FIG. 1C, and by reference number 140, the activity signature platform may associate state annotations with the patterns based on the state information. In some implementations, the state information may include the state annotations, where each state annotation may include an annotation designating one of the different activities of individuals. For example, the state annotations may include annotations designating that an individual is interval training, running, sleeping, resting, working at a desk, walking, and/or the like. As shown in FIG. 1C, the activity signature platform may associate a first state annotation (e.g., interval training) with a first pattern, may associate a second state annotation (e.g., running) with a second pattern, may associate a third state annotation (e.g., sleeping) with a third pattern, and/or the like. In this way, the activity signature platform may annotate or label activities of the individual based on the patterns identified in the normalized individual information.

Figure 1D:
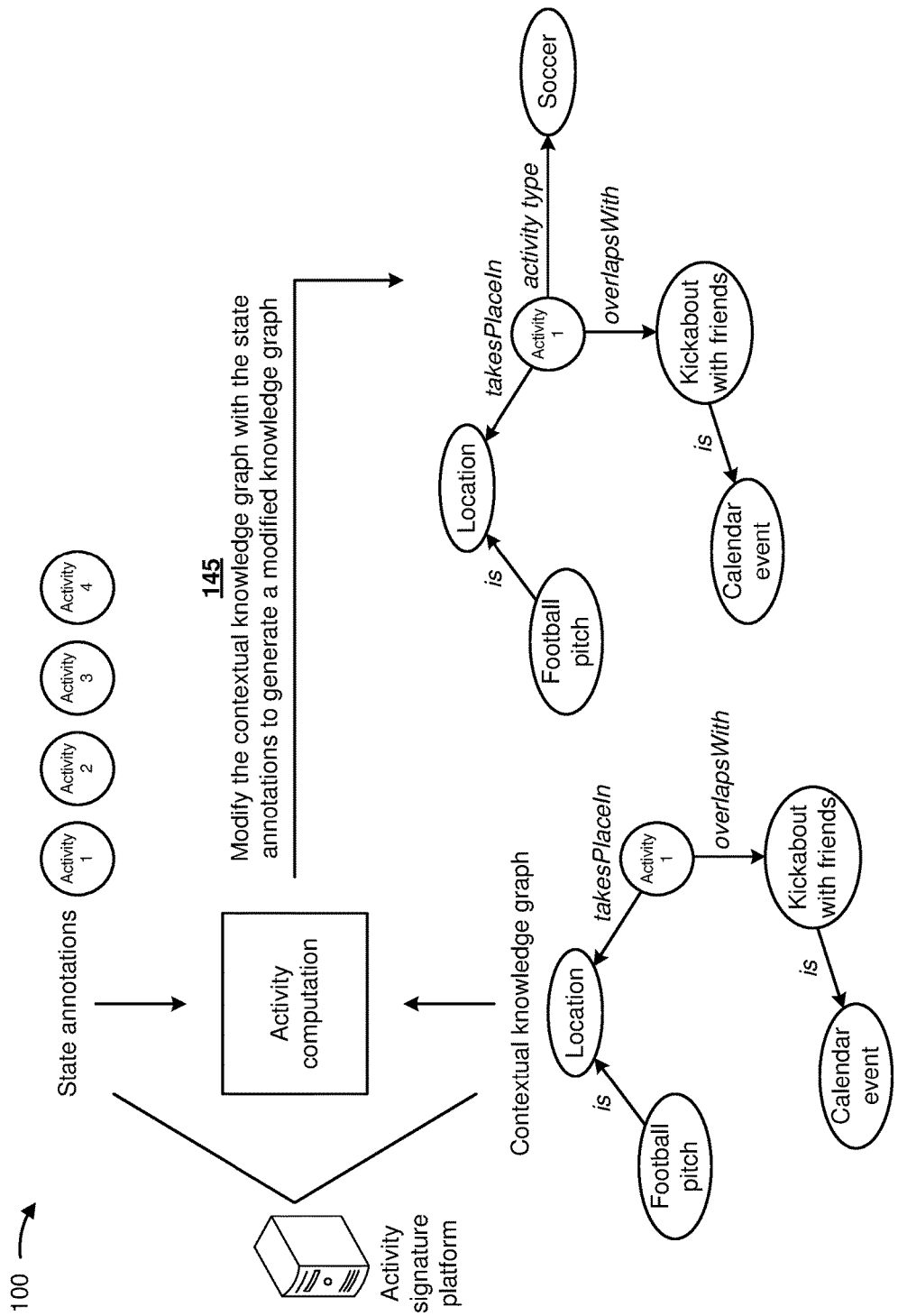

As shown in FIG. 1D, and by reference number 145, the activity signature platform may modify the contextual knowledge graph with the state annotations (e.g., associated with the patterns identified in the normalized individual information, such as activities 1, 2, 3, and 4) to generate a modified knowledge graph. For example, the contextual knowledge graph may include a first node associated with a football pitch, a second node associated with a location of the football pitch, a third node associated with a kickabout a soccer ball with friends, and a fourth node associated with a calendar event of the football pitch. A first state annotation may be associated with a first activity type (e.g., soccer). In some implementations, the activity signature platform may modify the contextual knowledge graph to associate the first state annotation with the contextual knowledge graph (e.g., since the contextual knowledge graph and the first state information (e.g., activity 1) relates to playing soccer). For example, as shown in FIG. 1D, the contextual knowledge graph may be modified to include a new node for the first state annotation (e.g., indicating a first activity type of soccer).

In some implementations, the activity signature platform may modify the contextual knowledge graph with other state annotations to generate the modified knowledge graph. For example, the activity signature platform may modify the contextual knowledge graph to associate one or more of a second state annotation, a third state annotation, and/or the like, with the contextual knowledge graph. In some implementations, the activity signature platform may infer an activity of the individual based on the modified knowledge graph.

Figure 1E:
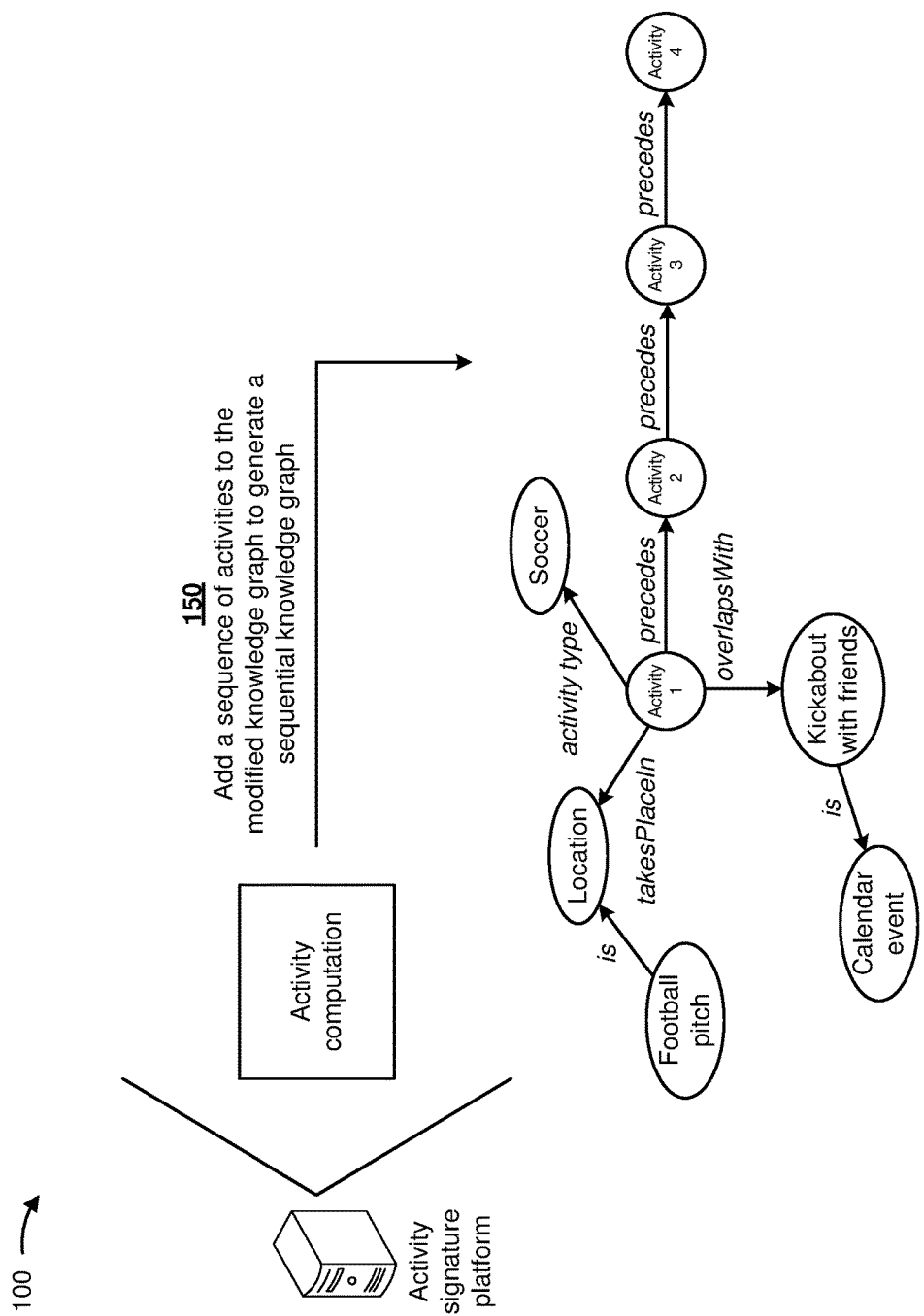

As shown in FIG. 1E, and by reference number 150, the activity signature platform may add a sequence of activities (e.g., represented by the state annotations) to the modified knowledge graph to generate a sequential knowledge graph. In some implementations, the activity signature platform may determine that the first activity type (e.g., soccer) occurs after a second activity type, the second activity type occurs after a third activity type, and the third activity type occurs after a fourth activity type. For example, if the second activity type is warming up, the third activity type is driving to a soccer field, and the fourth activity type is getting dressed in a soccer uniform, then getting dressed in the soccer uniform (e.g., the fourth activity type) precedes driving to the soccer field (e.g., the third activity type), which precedes warming up (e.g., the second activity type), which precedes soccer (e.g., the first activity type).

Figure 1F:
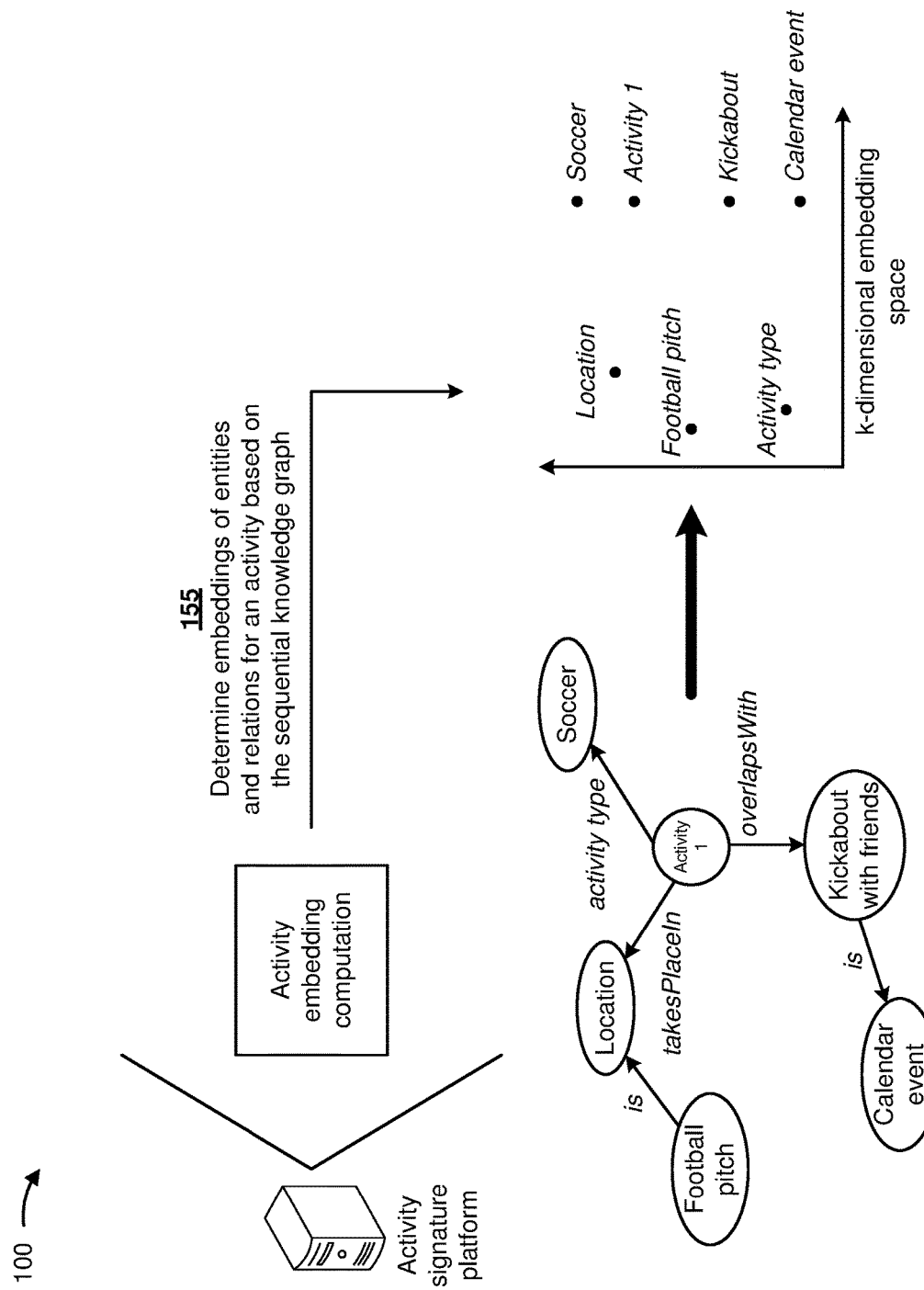

As shown in FIG. 1F, and by reference number 155, the activity signature platform may determine embeddings of entities and relations for an activity of the individual based on the sequential knowledge graph. In some implementations, the activity signature platform may utilize neural knowledge graph embeddings (e.g., embeddings used to compute semantic relatedness in a coherence-based semantic parser, and that utilizes deep structured semantic modeling to learn neural embeddings for all of the concepts) with the sequential knowledge graph to determine the embeddings. In some implementations, the embeddings may include points in a k-dimensional embedding space, and may provide latent semantic representations for structured knowledge in the sequential knowledge graph. In some implementations, the embeddings may enable direct explicit relational inferences among entities via simple calculation of embedding vectors, and may be effective at highlighting key concepts underlying sophisticated human language.

In some implementations, the activity signature platform may convert entities (e.g., nodes) and relations (e.g., links or edges) of the sequential knowledge graph into points in a k-dimensional metric space. For example, as shown in FIG. 1F, the embeddings may include points in a k-dimensional metric space (e.g., shown as a graph in two dimensions for simplicity). In some implementations, the activity signature platform may minimize a loss function to learn parameters that best discriminate positive statements from negative statements. In such implementations, the loss function may include a function that maps a statement onto a real number that represents the likelihood of that statement to be true. In such implementations, the loss function may include a pairwise margin-based loss function, a negative log-likelihood loss function, and/or the like. In some implementations, the activity signature platform may assign scores to statements of the sequential knowledge graph in order to aid the loss function in determining how well the sequential knowledge graph tells positive statements from negative statements. In some implementations, the activity signature platform may minimize the loss function in order to determine optimal parameters of the sequential knowledge graph (e.g., the embeddings).

Figure 1G:
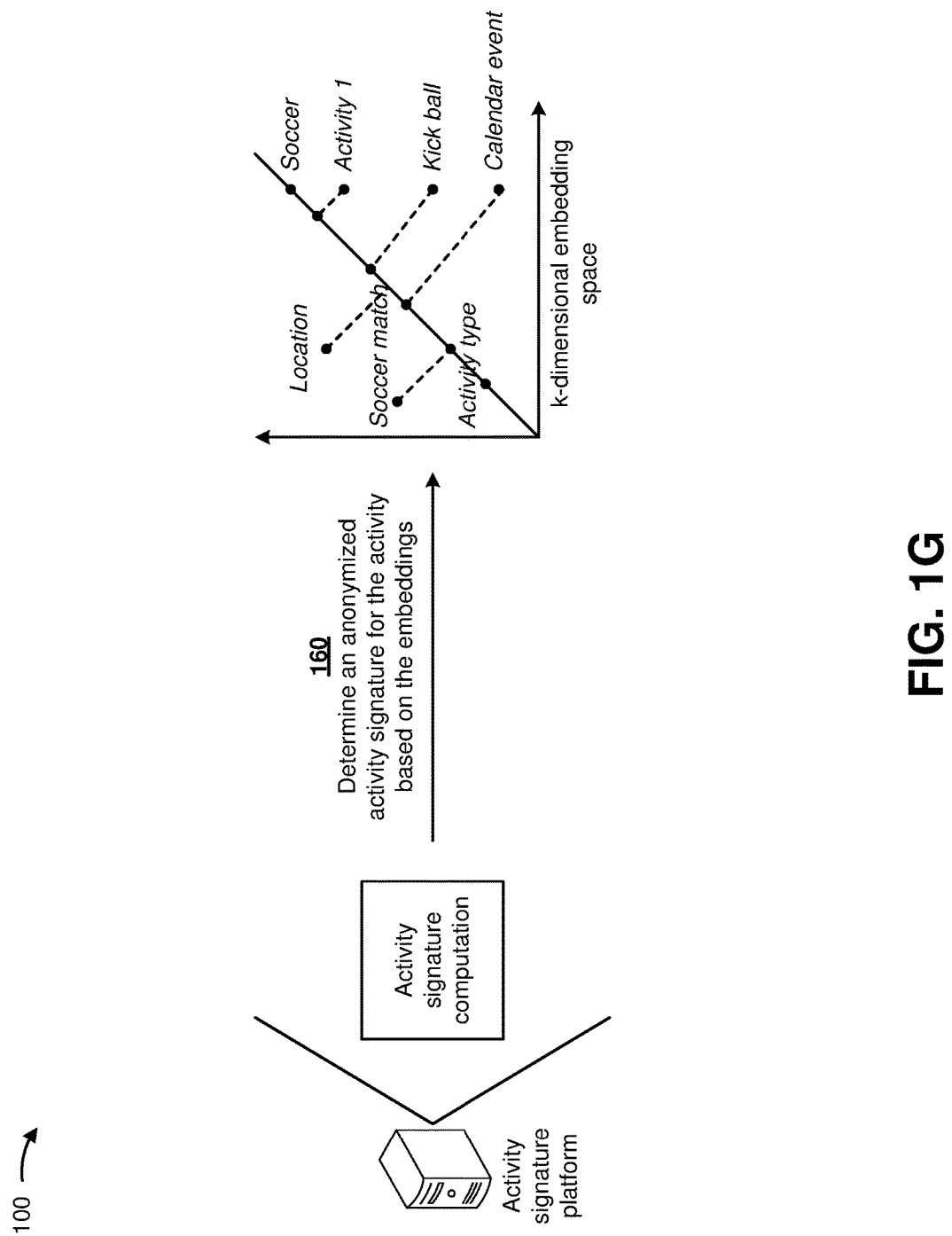

As shown in FIG. 1G, and by reference number 160, the activity signature platform may determine an anonymized activity signature for the activity of the individual based on the embeddings. In some implementations, the activity signature platform may apply a principal component analysis (PCA) to the embeddings ($e_i$) for an activity ($A_i$) in order to determine a first component ($Y_{Ai}$) (e.g., a component, as shown by the straight line in FIG. 1G, on which projections of the embeddings have a greatest amount of variance), as follows:

$$Y_{Ai} = PCA(\{e_i\}_{Ai}, 1).$$

The principal component analysis may reduce the dimensions of the embeddings to a low dimensional space and a vector ($Y_{Ai}$) in that space. The activity signature platform may determine the anonymized activity signature ($S_{Ai}$) for the activity based on a norm of the first component ($Y_{Ai}$) (e.g., as shown by the projected points on the line in FIG. 1G), as follows:

$$S_{Ai} = \|Y_{Ai}\|_2.$$

The anonymized activity signature ($S_{Ai}$) may include a single vector that is anonymized form of the individual information. In some implementations, the activity signature platform may determine anonymized activity signatures for all activities performed by the individual based on the embeddings.

Figure 1H:
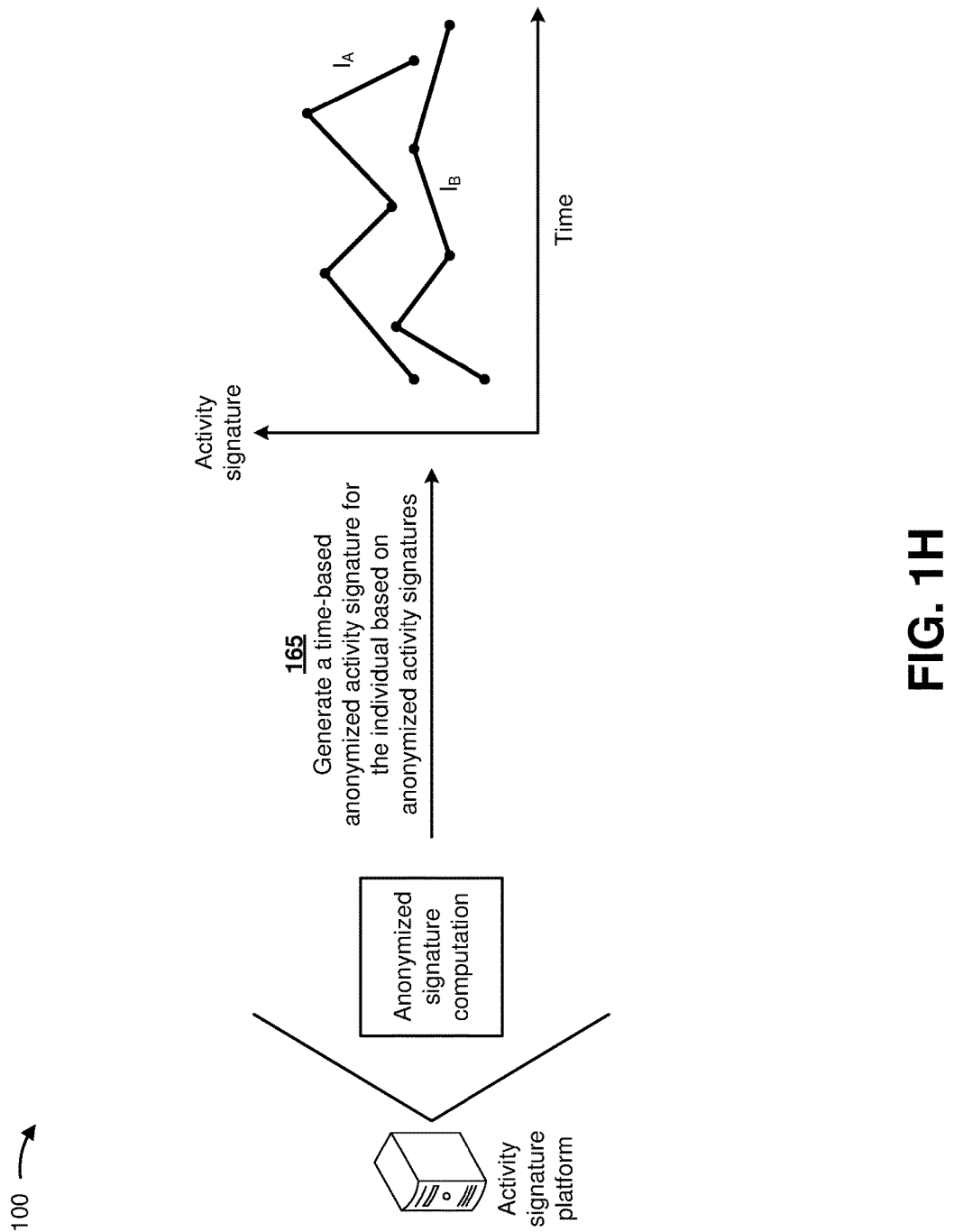

As shown in FIG. 1H, and by reference number 165, the activity signature platform may generate a time-based anonymized activity signature for the individual based on anonymized activity signatures. In some implementations, the activity signature platform may combine or concatenate the anonymized activity signatures for the individual to generate the time-based anonymized activity signature. For example, as shown in FIG. 1H, the activity signature platform may determine a first time-based anonymized activity signature for a first individual ($I_A$), and a second time-based anonymized activity signature for a second individual ($I_B$). A first point of the first time-based anonymized activity signature may correspond to a first anonymized activity signature of the first individual, a second point of the first time-based anonymized activity signature may correspond to a second anonymized activity signature of the first individual, and/or the like. A first point of the second time-based anonymized activity signature may correspond to a first anonymized activity signature of the first individual, a second point of the second time-based anonymized activity signature may correspond to a second anonymized activity signature of the second individual, and/or the like.

In this way, the activity signature platform may generate a time-based anonymized activity signature that is unique to an individual for a pre-determined period of time, and that provides an anonymized manner of storing some of the original individual information. The time-based anonymized activity signature may permit similarities and/or differences between individuals to be determined. Furthermore, the activity signature platform may convert the individual information from an embedding space into a single vector, and may calculate a magnitude of the single vector to create a digital signature for each activity in a sequence and to create the time-based anonymized activity signature for the sequence.

Figure 1I:
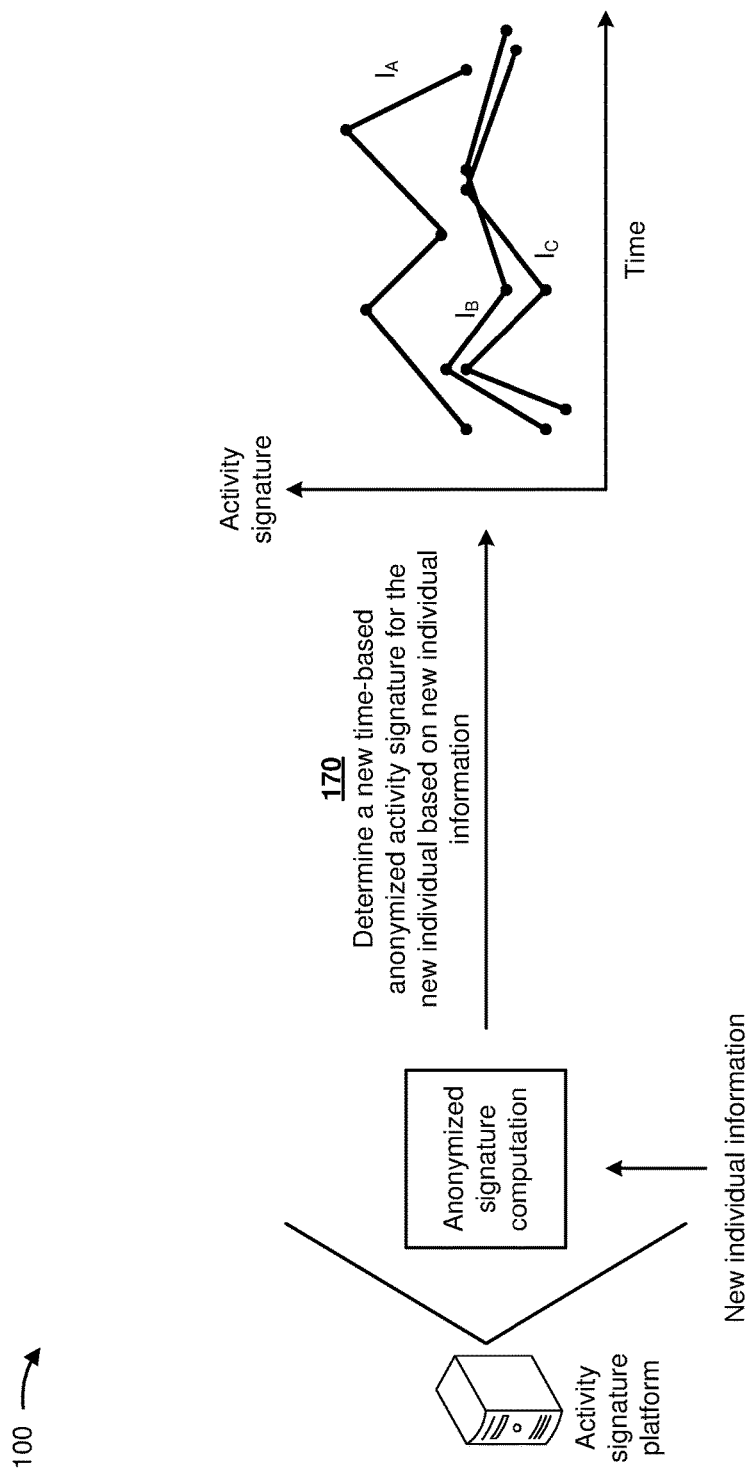

As shown in FIG. 1I, and by reference number 170, the activity signature platform may receive new individual information (e.g., associated with a new individual), and may determine a new time-based anonymized activity signature for the new individual based on the new individual information. In some implementations, the activity signature platform may determine the new time-based anonymized activity signature in a similar manner described above for the time-based anonymized activity signature. In some implementations, the activity signature platform may compare the individual information and the new individual information associated with the new individual based on the time-based anonymized activity signature and the new time-based anonymized activity signature, and without divulging the individual information and/or the new individual information.

In some implementations, the activity signature platform may utilize the time-based anonymized activity signature to perform one or more actions. In one example, the activity signature platform may compare the time-based anonymized activity signature and a new time-based anonymized activity signature (e.g., associated with a new individual) to anonymously determine similarities and/or differences between the individual and the new individual. In another example, the activity signature platform may configure the wearable device associated with the individual based on the time-based anonymized activity signature to improve tracking of the activities of the individual. In still another example, the activity signature platform may provide information indicating a recommended activity (e.g., running) for the individual based on the time-based anonymized activity signature so that the individual may become healthier (e.g., improve blood pressure). In another example, the activity signature platform may provide information indicating recommended activities for another individual based on the time-based anonymized activity signature (e.g., so that the other individual may become as healthy as the individual).

In this way, several different stages of the process for determining anonymized temporal activity signatures of individuals are automated, which may remove human subjectivity and waste from the process, and which may improve speed and efficiency of the process and conserve computing resources (e.g., processing resources, memory resources, and/or the like). Furthermore, implementations described herein use a rigorous, computerized process to perform tasks or roles that were not previously performed or were previously performed using subjective human intuition or input. For example, currently there does not exist a technique that automatically determines anonymized temporal activity signatures of individuals. Finally, automating the process for determining anonymized temporal activity signatures of individuals conserves computing resources (e.g., processing resources, memory resources, and/or the like) that would otherwise be wasted in attempting to anonymize personal information (e.g., the individual information) of individuals.

As indicated above, FIGS. 1A-1I are provided merely as examples. Other examples are possible and may differ from what was described with regard to FIGS. 1A-1I.

Figure 2:
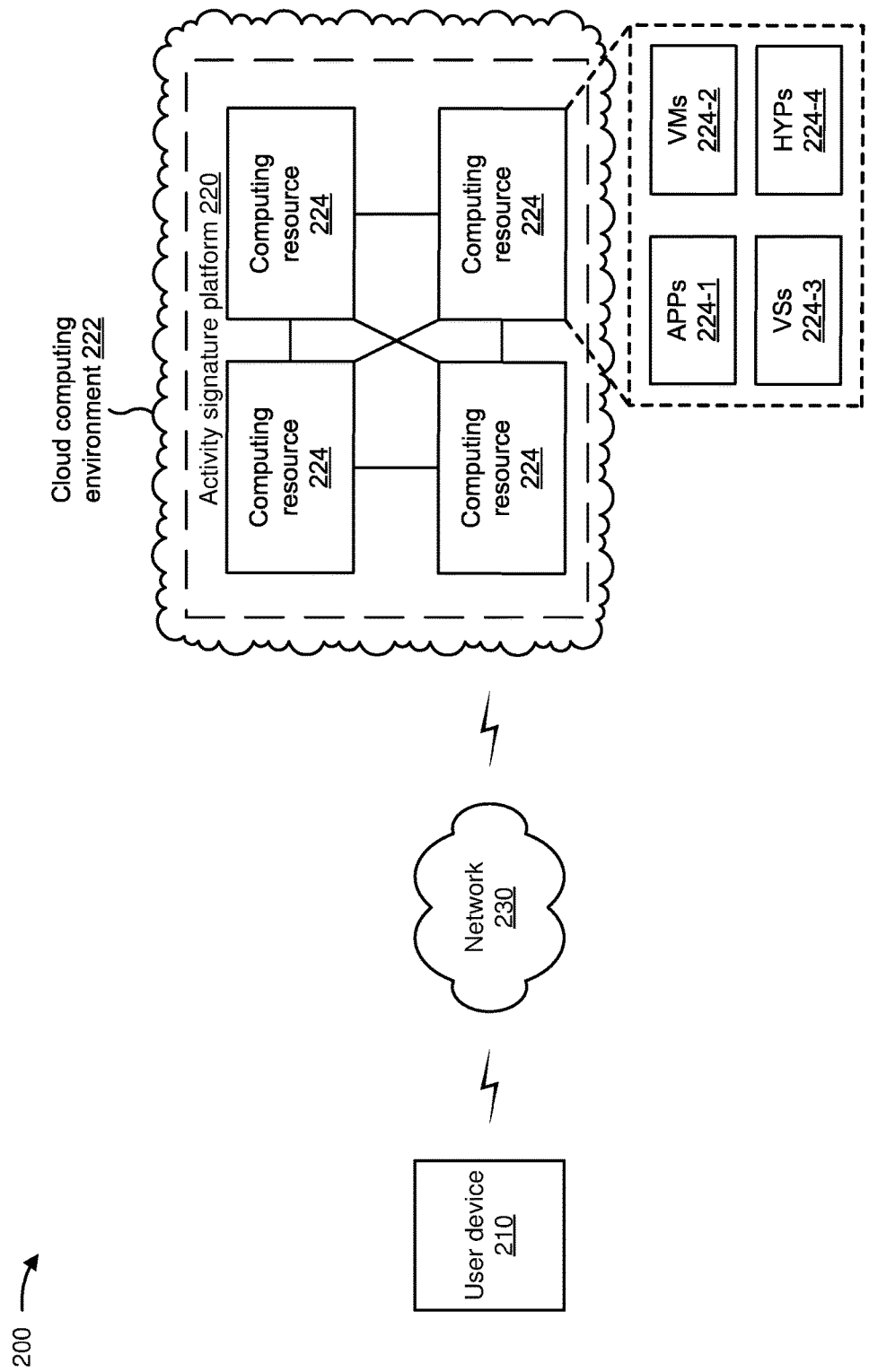
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, an activity signature platform 220, and a network 230. Devices of environment 200 may interconnect via wired connections, wireless connections, or a combination of wired and wireless connections.

User device 210 includes one or more devices capable of receiving, generating, storing, processing, and/or providing information, such as information described herein. For example, user device 210 may include a mobile phone (e.g., a smart phone, a radiotelephone, etc.), a laptop computer, a tablet computer, a desktop computer, a handheld computer, a gaming device, a wearable communication device (e.g., a smart watch, a pair of smart glasses, a heart rate monitor, a fitness tracker, smart clothing, smart jewelry, a head mounted display, etc.), or a similar type of device. In some implementations, user device 210 may receive information from and/or transmit information to activity signature platform 220.

Activity signature platform 220 includes one or more devices that determines anonymized temporal activity signatures of individuals. In some implementations, activity signature platform 220 may be designed to be modular such that certain software components may be swapped in or out depending on a particular need. As such, activity signature platform 220 may be easily and/or quickly reconfigured for different uses. In some implementations, activity signature platform 220 may receive information from and/or transmit information to one or more user devices 210.

In some implementations, as shown, activity signature platform 220 may be hosted in a cloud computing environment 222. Notably, while implementations described herein describe activity signature platform 220 as being hosted in cloud computing environment 222, in some implementations, activity signature platform 220 may not be cloud-based (i.e., may be implemented outside of a cloud computing environment) or may be partially cloud-based.

Cloud computing environment 222 includes an environment that hosts activity signature platform 220. Cloud computing environment 222 may provide computation, software, data access, storage, etc. services that do not require end-user knowledge of a physical location and configuration of system(s) and/or device(s) that hosts activity signature platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host activity signature platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by user device 210. Application 224-1 may eliminate a need to install and execute the software applications on user device 210. For example, application 224-1 may include software associated with activity signature platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., a user of user device 210 or an operator of activity signature platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
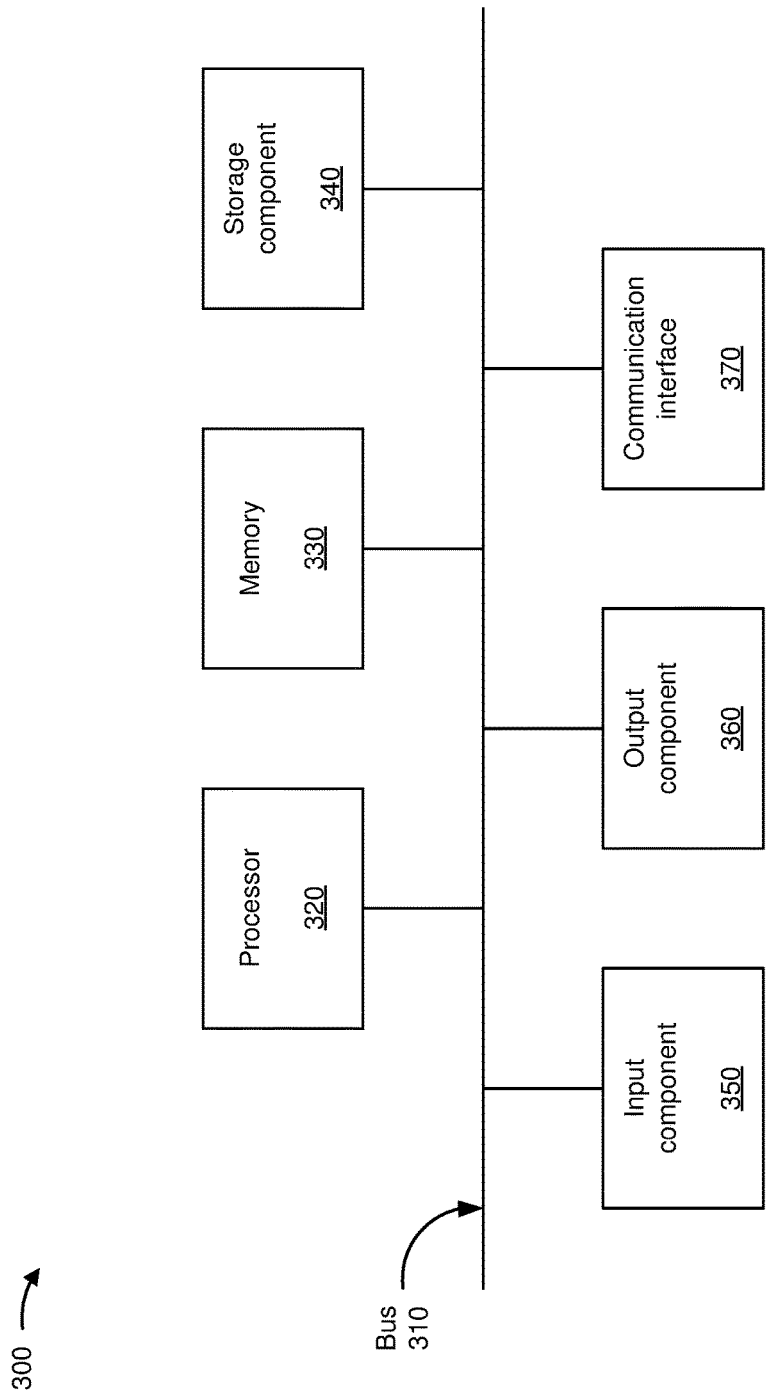
FIG. 3 is a diagram of example components of one or more devices of FIG. 2.

FIG. 3 is a diagram of example components of a device 300. Device 300 may correspond to user device 210, activity signature platform 220, and/or computing resource 224. In some implementations, user device 210, activity signature platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
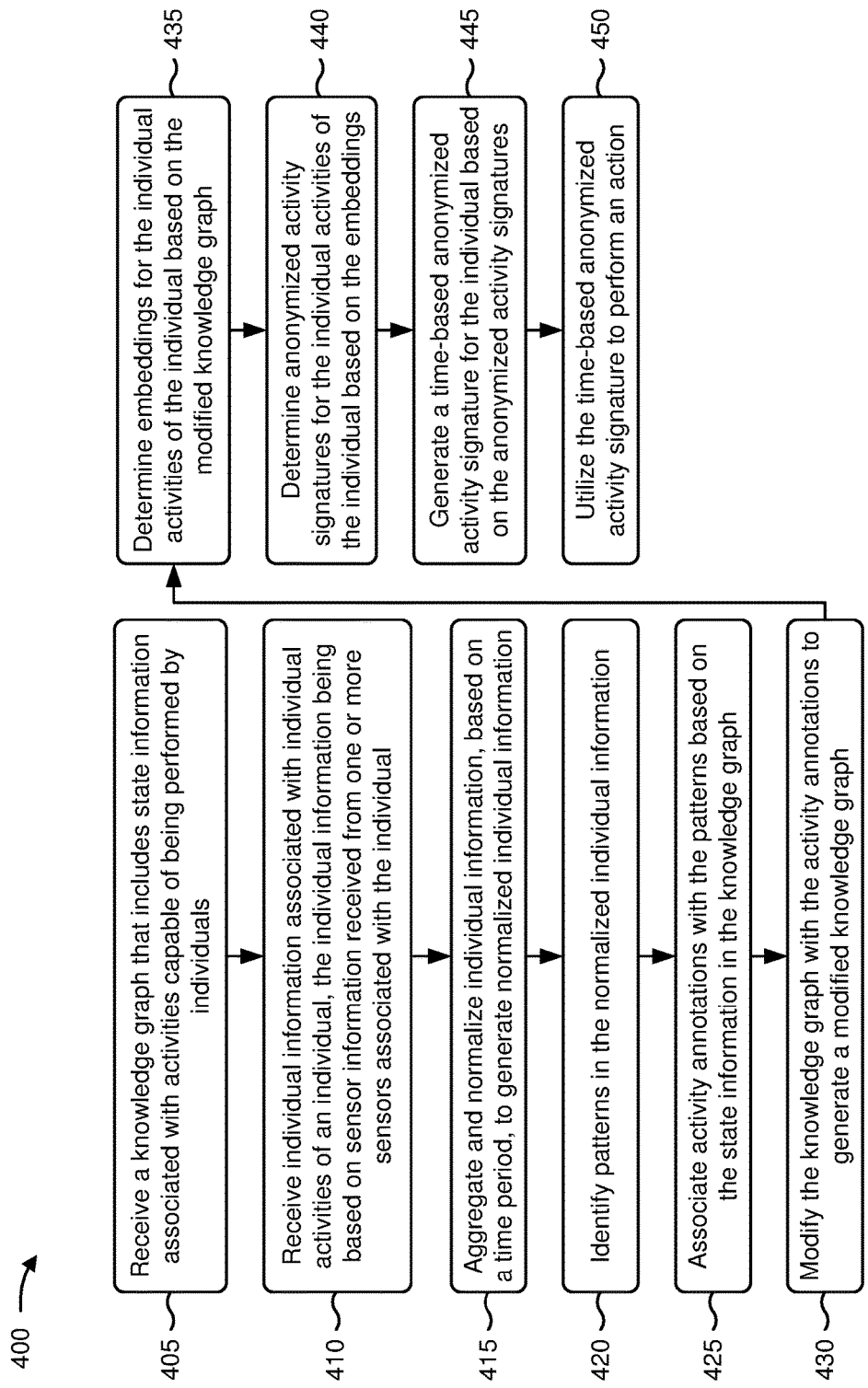
FIGS. 4-6 are flow charts of example processes for determining anonymized temporal activity signatures of individuals.

FIG. 4 is a flow chart of an example process 400 for determining anonymized temporal activity signatures of individuals. In some implementations, one or more process blocks of FIG. 4 may be performed by an activity signature platform (e.g., activity signature platform 220). In some implementations, one or more process blocks of FIG. 4 may be performed by another device or a group of devices separate from or including the activity signature platform, such as a user device (e.g., user device 210).

As shown in FIG. 4, process 400 may include receiving a knowledge graph that includes state information associated with activities capable of being performed by individuals (block 405). For example, the activity signature platform (e.g., using computing resource 224, processor 320, communication interface 370, and/or the like) may receive a knowledge graph and state information associated with activities capable of being performed by individuals, as described above in connection with FIGS. 1A-2.

As further shown in FIG. 4, process 400 may include receiving individual information associated with individual activities of an individual, the individual information being based on sensor information received from one or more sensors associated with the individual (block 410). For example, the activity signature platform (e.g., using computing resource 224, processor 320, communication interface 370, and/or the like) may receive individual information associated with individual activities of an individual, as described above in connection with FIGS. 1A-2. In some implementations, the individual information may be based on sensor information received from one or more sensors associated with the individual.

As further shown in FIG. 4, process 400 may include aggregating and normalizing the individual information, based on a time period, to generate normalized individual information (block 415). For example, the activity signature platform (e.g., using computing resource 224, processor 320, storage component 340, and/or the like) may aggregate and normalize the individual information, based on a time period, to generate normalized individual information, as described above in connection with FIGS. 1A-2.

As further shown in FIG. 4, process 400 may include identifying patterns in the normalized individual information (block 420). For example, the activity signature platform (e.g., using computing resource 224, processor 320, memory 330, storage component 340, and/or the like) may identify patterns in the normalized individual information, as described above in connection with FIGS. 1A-2.

As further shown in FIG. 4, process 400 may include associating activity annotations with the patterns based on the state information in the knowledge graph, wherein a plurality of activity annotations is associated to create a temporal sequence of activities (block 425). For example, the activity signature platform (e.g., using computing resource 224, processor 320, memory 330, and/or the like) may associate activity annotations with the patterns based on the state information in the knowledge graph, as described above in connection with FIGS. 1A-2. In some implementations, a plurality of activity annotations may be associated to create a temporal sequence of activities.

As further shown in FIG. 4, process 400 may include modifying the knowledge graph with the activity annotations to generate a modified knowledge graph (block 430). For example, the activity signature platform (e.g., using computing resource 224, processor 320, storage component 340, and/or the like) may modify the knowledge graph with the activity annotations to generate a modified knowledge graph, as described above in connection with FIGS. 1A-2.

As further shown in FIG. 4, process 400 may include determining embeddings for the individual activities of the individual based on the modified knowledge graph (block 435). For example, the activity signature platform (e.g., using computing resource 224, processor 320, storage component 340, and/or the like) may determine embeddings for the individual activities of the individual based on the modified knowledge graph, as described above in connection with FIGS. 1A-2.

As further shown in FIG. 4, process 400 may include determining anonymized activity signatures for the individual activities of the individual based on the embeddings by determining a vector element based on the embeddings, determining a magnitude parameter of the vector element to create a plurality of intermediate activity signatures, each intermediate activity signature being associated with an activity in the temporal sequence of activities, and aggregating the plurality of intermediate activity signatures to create an overall anonymized activity signature for the temporal sequence of activities (block 440). For example, the activity signature platform (e.g., using computing resource 224, processor 320, memory 330, and/or the like) may determine anonymized activity signatures for the individual activities of the individual based on the embeddings by determining a vector element based on the embeddings, determining a magnitude parameter of the vector element to create a plurality of intermediate activity signatures, each intermediate activity signature being associated with an activity in the temporal sequence of activities, and aggregating the plurality of intermediate activity signatures to create an overall anonymized activity signature for the temporal sequence of activities, as described above in connection with FIGS. 1A-2.

As further shown in FIG. 4, process 400 may include generating a time-based anonymized activity signature for the individual based on the anonymized activity signatures (block 445). For example, the activity signature platform (e.g., using computing resource 224, processor 320, storage component 340, and/or the like) may generate a time-based anonymized activity signature for the individual based on the anonymized activity signatures, as described above in connection with FIGS. 1A-2.

As further shown in FIG. 4, process 400 may include utilizing the time-based anonymized activity signature to perform an action (block 450). For example, the activity signature platform (e.g., using computing resource 224, processor 320, memory 330, communication interface 370, and/or the like) may utilize the time-based anonymized activity signature to perform an action, as described above in connection with FIGS. 1A-2.

Process 400 may include additional implementations, such as any single implementation or any combination of implementations described below and/or described with regard to any other process described herein.

In some implementations, the activity signature platform, when utilizing the time-based anonymized activity signature to perform the action, may determine a new time-based anonymized activity signature for a new individual based on the time-based anonymized activity signature, may configure the one or more sensors associated with the individual based on the time-based anonymized activity signature to improve tracking of the activities of the individual, may provide information indicating a recommended activity for the individual based on the time-based anonymized activity signature, may provide information indicating recommended activities for another individual based on the time-based anonymized activity signature, and/or the like.

In some implementations, the knowledge graph may include nodes that represent the activities, and may include links representing relations between the activities. In some implementations, the activity signature platform, when determining the anonymized activity signatures for the individual activities, may utilize the embeddings to calculate activity signatures for the individual activities, and may apply a principal component analysis to the activity signatures to generate the anonymized activity signatures. In some implementations, the one or more sensors may include a heart rate monitor, smart glasses, a fitness tracker, a smart watch, smart clothing, smart jewelry, a head mounted display, and/or the like.

In some implementations, the activity signature platform, when utilizing the time-based anonymized activity signature to perform the action, may compare the individual information associated with the individual and information associated with a new individual based on the time-based anonymized activity signature and without divulging the individual information. In some implementations, the activity signature platform, when determining the anonymized activity signatures for the individual activities, may determine a single anonymized activity signature for each of the individual activities of the individual based on the embeddings.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
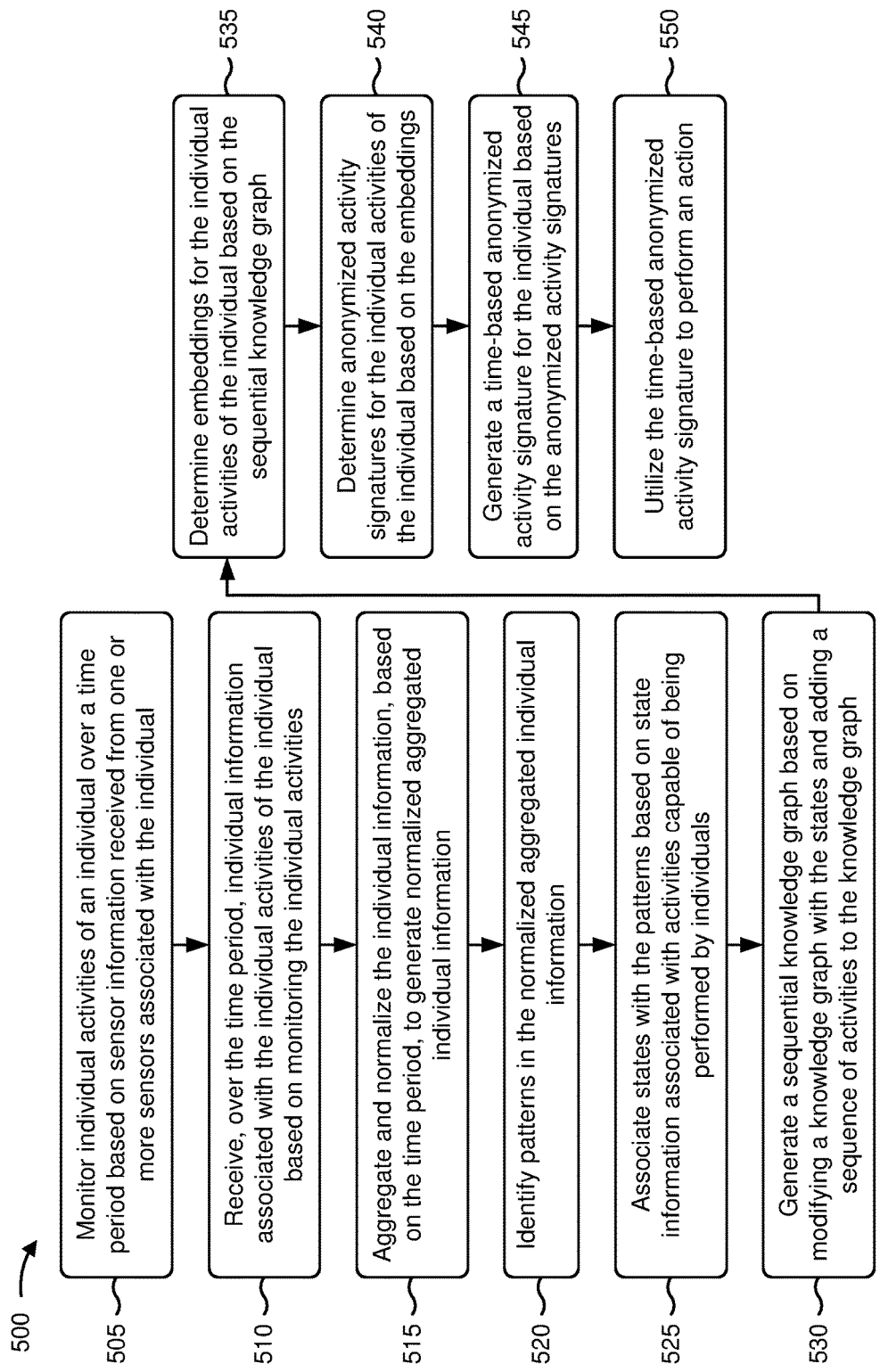

FIG. 5 is a flow chart of an example process 500 for determining anonymized temporal activity signatures of individuals. In some implementations, one or more process blocks of FIG. 5 may be performed by an activity signature platform (e.g., activity signature platform 220). In some implementations, one or more process blocks of FIG. 5 may be performed by another device or a group of devices separate from or including the activity signature platform, such as a user device (e.g., user device 210).

As shown in FIG. 5, process 500 may include monitoring individual activities of an individual over a time period based on sensor information received from one or more sensors associated with the individual (block 505). For example, the activity signature platform (e.g., using computing resource 224, processor 320, communication interface 370, and/or the like) may monitor individual activities of an individual over a time period based on sensor information received from one or more sensors associated with the individual, as described above in connection with FIGS. 1A-2.

As further shown in FIG. 5, process 500 may include receiving, over the time period, individual information associated with the individual activities of the individual based on monitoring the individual activities (block 510). For example, the activity signature platform (e.g., using computing resource 224, processor 320, communication interface 370, and/or the like) may receive, over the time period, individual information associated with the individual activities of the individual based on monitoring the individual activities, as described above in connection with FIGS. 1A-2.

As further shown in FIG. 5, process 500 may include aggregating and normalizing the individual information, based on the time period, to generate normalized aggregated individual information (block 515). For example, the activity signature platform (e.g., using computing resource 224, processor 320, memory 330, and/or the like) may aggregate and normalize the individual information, based on the time period, to generate normalized aggregated individual information, as described above in connection with FIGS. 1A-2.

As further shown in FIG. 5, process 500 may include identifying patterns in the normalized aggregated individual information (block 520). For example, the activity signature platform (e.g., using computing resource 224, processor 320, memory 330, storage component 340, and/or the like) may identify patterns in the normalized aggregated individual information, as described above in connection with FIGS. 1A-2.

As further shown in FIG. 5, process 500 may include associating states with the patterns based on state information associated with activities capable of being performed by individuals (block 525). For example, the activity signature platform (e.g., using computing resource 224, processor 320, memory 330, and/or the like) may associate states with the patterns based on state information associated with activities capable of being performed by individuals, as described above in connection with FIGS. 1A-2.

As further shown in FIG. 5, process 500 may include generating a sequential knowledge graph based on modifying a knowledge graph with the states and adding a sequence of activities to the knowledge graph (block 530). For example, the activity signature platform (e.g., using computing resource 224, processor 320, storage component 340, and/or the like) may generate a sequential knowledge graph based on modifying a knowledge graph with the states and adding a sequence of activities to the knowledge graph, as described above in connection with FIGS. 1A-2.

As further shown in FIG. 5, process 500 may include determining embeddings for the individual activities of the individual based on the sequential knowledge graph (block 535). For example, the activity signature platform (e.g., using computing resource 224, processor 320, memory 330, and/or the like) may determine embeddings for the individual activities of the individual based on the sequential knowledge graph, as described above in connection with FIGS. 1A-2.

As further shown in FIG. 5, process 500 may include determining anonymized activity signatures for the individual activities of the individual based on the embeddings (block 540). For example, the activity signature platform (e.g., using computing resource 224, processor 320, storage component 340, and/or the like) may determine anonymized activity signatures for the individual activities of the individual based on the embeddings, as described above in connection with FIGS. 1A-2.

As further shown in FIG. 5, process 500 may include generating a time-based anonymized activity signature for the individual based on the anonymized activity signatures (block 545). For example, the activity signature platform (e.g., using computing resource 224, processor 320, memory 330, and/or the like) may generate a time-based anonymized activity signature for the individual based on the anonymized activity signatures, as described above in connection with FIGS. 1A-2.

As further shown in FIG. 5, process 500 may include utilizing the time-based anonymized activity signature to perform an action (block 550). For example, the activity signature platform (e.g., using computing resource 224, processor 320, memory 330, communication interface 370, and/or the like) may utilize the time-based anonymized activity signature to perform an action, as described above in connection with FIGS. 1A-2.

Process 500 may include additional implementations, such as any single implementation or any combination of implementations described below and/or described with regard to any other process described herein.

In some implementations, a portion of the individual information may be received from the one or more sensors associated with the individual, and the one or more sensors may include a heart rate monitor, smart glasses, a fitness tracker, a smart watch, smart clothing, smart jewelry, and/or a head mounted display.

In some implementations, the activity signature platform, when generating the sequential knowledge graph, may combine the states to determine activity types, may modify the activity types with the knowledge graph, and may create the sequence of activities based on modifying the activity types.

In some implementations, the activity signature platform, when determining the embeddings for the individual activities, may utilize the sequential knowledge graph and a neural network model to determine the embeddings for the individual activities.

In some implementations, the activity signature platform, when determining the anonymized activity signatures for the individual activities, may utilize the embeddings to calculate activity signatures for the individual activities, and may apply a principal component analysis to the activity signatures to generate the anonymized activity signatures.

In some implementations, the activity signature platform, when generating the time-based anonymized activity signature for the individual, may concatenate the anonymized activity signatures for the individual activities to generate the time-based anonymized activity signature for the individual.

In some implementations, the activity signature platform, when utilizing the time-based anonymized activity signature to perform the action, may determine a new time-based anonymized activity signature for a new individual, and may compare the individual information and new individual information associated with the new individual based on the time-based anonymized activity signature and the new time-based anonymized activity signature.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
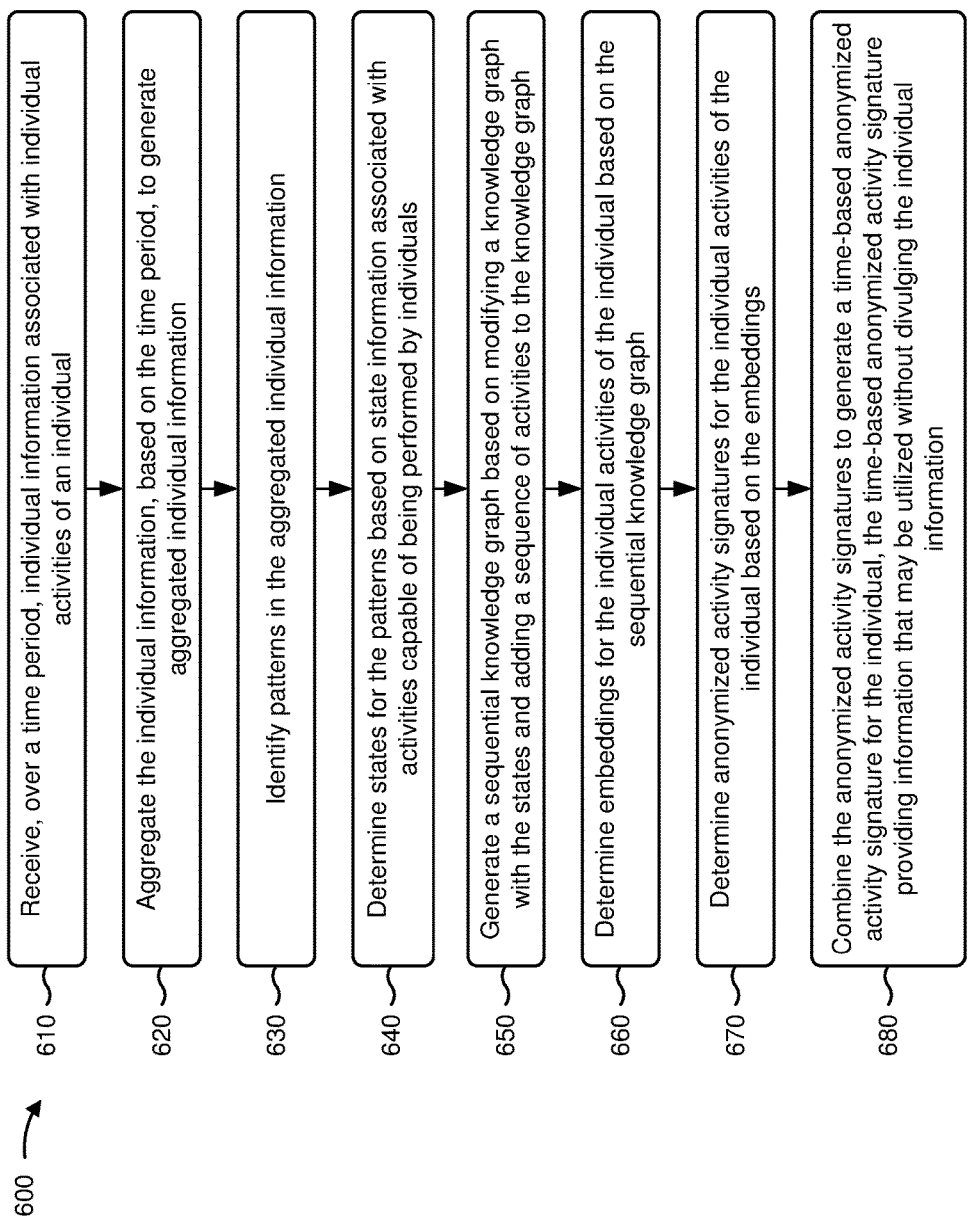

FIG. 6 is a flow chart of an example process 600 for determining anonymized temporal activity signatures of individuals. In some implementations, one or more process blocks of FIG. 6 may be performed by an activity signature platform (e.g., activity signature platform 220). In some implementations, one or more process blocks of FIG. 6 may be performed by another device or a group of devices separate from or including the activity signature platform, such as a user device (e.g., user device 210).

As shown in FIG. 6, process 600 may include receiving, over a time period, individual information associated with individual activities of an individual (block 610). For example, the activity signature platform (e.g., using computing resource 224, processor 320, storage component 340, communication interface 370, and/or the like) may receive, over a time period, individual information associated with individual activities of an individual, as described above in connection with FIGS. 1A-2.

As further shown in FIG. 6, process 600 may include aggregating the individual information, based on the time period, to generate aggregated individual information (block 620). For example, the activity signature platform (e.g., using computing resource 224, processor 320, memory 330, and/or the like) may aggregate the individual information, based on the time period, to generate aggregated individual information, as described above in connection with FIGS. 1A-2.

As further shown in FIG. 6, process 600 may include identifying patterns in the aggregated individual information (block 630). For example, the activity signature platform (e.g., using computing resource 224, processor 320, storage component 340, and/or the like) may identify patterns in the aggregated individual information, as described above in connection with FIGS. 1A-2.

As further shown in FIG. 6, process 600 may include determining states for the patterns based on state information associated with activities capable of being performed by individuals (block 640). For example, the activity signature platform (e.g., using computing resource 224, processor 320, memory 330, and/or the like) may determine states for the patterns based on state information associated with activities capable of being performed by individuals, as described above in connection with FIGS. 1A-2.

As further shown in FIG. 6, process 600 may include generating a sequential knowledge graph based on modifying a knowledge graph with the states and adding a sequence of activities to the knowledge graph (block 650). For example, the activity signature platform (e.g., using computing resource 224, processor 320, memory 330, storage component 340, and/or the like) may generate a sequential knowledge graph based on modifying a knowledge graph with the states and adding a sequence of activities to the knowledge graph, as described above in connection with FIGS. 1A-2.

As further shown in FIG. 6, process 600 may include determining embeddings for the individual activities of the individual based on the sequential knowledge graph (block 660). For example, the activity signature platform (e.g., using computing resource 224, processor 320, memory 330, and/or the like) may determine embeddings for the individual activities of the individual based on the sequential knowledge graph, as described above in connection with FIGS. 1A-2.

As further shown in FIG. 6, process 600 may include determining anonymized activity signatures for the individual activities of the individual based on the embeddings (block 670). For example, the activity signature platform (e.g., using computing resource 224, processor 320, storage component 340, and/or the like) may determine anonymized activity signatures for the individual activities of the individual based on the embeddings, as described above in connection with FIGS. 1A-2.

As further shown in FIG. 6, process 600 may include combining the anonymized activity signatures to generate a time-based anonymized activity signature for the individual, the time-based anonymized activity signature providing information that may be utilized without divulging the individual information (block 680). For example, the activity signature platform (e.g., using computing resource 224, processor 320, memory 330, and/or the like) may combine the anonymized activity signatures to generate a time-based anonymized activity signature for the individual, as described above in connection with FIGS. 1A-2. In some implementations, the time-based anonymized activity signature may provide information that may be utilized without divulging the individual information.

Process 600 may include additional implementations, such as any single implementation or any combination of implementations described below and/or described with regard to any other process described herein.

In some implementations, the activity signature platform may utilize the time-based anonymized activity signature to perform an action. In some implementations, the activity signature platform, when utilizing the time-based anonymized activity signature to perform the action, may determine a new time-based anonymized activity signature for a new individual, and may compare the individual information and new individual information associated with the new individual based on the time-based anonymized activity signature and the new time-based anonymized activity signature. In some implementations, the activity signature platform, when determining the anonymized activity signatures, may utilize the embeddings to calculate activity signatures for the individual activities, and may apply a principal component analysis to the activity signatures to generate the anonymized activity signatures.

In some implementations, the activity signature platform, when generating the sequential knowledge graph, may combine the states to determine activity types, may modify the activity types with the knowledge graph, and may create the sequence of activities based on modifying the activity types. In some implementations, the activity signature platform, when determining the anonymized activity signatures for the individual activities, may utilize the embeddings to calculate activity signatures for the individual activities, and may apply a principal component analysis to the activity signatures to generate the anonymized activity signatures.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Some implementations described herein provide an activity signature platform that determines anonymized temporal activity signatures of individuals. For example, the activity signature platform may receive, over a time period, individual information associated with individual activities of an individual, and may aggregate the individual information, based on the time period, to generate aggregated individual information. The activity signature platform may identify patterns in the aggregated individual information, and may determine states for the patterns based on state information associated with activities capable of being performed by individuals. The activity signature platform may generate a sequential knowledge graph based on modifying a knowledge graph with the states and adding a sequence of activities to the knowledge graph, and may determine embeddings for the individual activities of the individual based on the sequential knowledge graph. The activity signature platform may determine anonymized activity signatures for the individual activities of the individual based on the embeddings, and may combine the anonymized activity signatures to generate a time-based anonymized activity signature for the individual, wherein the time-based anonymized activity signature providing information that may be utilized without divulging the individual information.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Certain user interfaces have been described herein and/or shown in the figures. A user interface may include a graphical user interface, a non-graphical user interface, a text-based user interface, or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
one or more memories; and
one or more processors, communicatively coupled to the one or more memories, to:
receive a knowledge graph that includes state information associated with activities capable of being performed by individuals;
receive individual information associated with individual activities of an individual,
the individual information being based on sensor information received from one or more sensors associated with the individual;
aggregate and normalize the individual information, based on a time period, to generate normalized individual information;
identify patterns in the normalized individual information;
associate activity annotations with the patterns based on the state information in the knowledge graph, wherein a plurality of the activity annotations is associated to create a temporal sequence of activities;
modify the knowledge graph with the activity annotations to generate a modified knowledge graph;
determine embeddings for the individual activities of the individual based on the modified knowledge graph;
determine anonymized activity signatures for the individual activities of the individual based on the embeddings,
wherein the one or more processors, when determining the anonymized activity signatures, are to
determine a vector element based on the embeddings,
determine a magnitude parameter of the vector element to create a plurality of intermediate activity signatures, each intermediate activity signature being associated with an activity in the temporal sequence of activities, and
aggregate the plurality of intermediate activity signatures to create an overall anonymized activity signature for the temporal sequence of activities;
generate a time-based anonymized activity signature for the individual based on the anonymized activity signatures; and
utilize the time-based anonymized activity signature to perform an action.

2. The device of claim 1, wherein the one or more processors, when utilizing the time-based anonymized activity signature to perform the action, are to one or more of:
determine a new time-based anonymized activity signature for a new individual based on the time-based anonymized activity signature,
configure the one or more sensors associated with the individual based on the time-based anonymized activity signature to improve tracking of the activities of the individual,
provide information indicating a recommended activity for the individual based on the time-based anonymized activity signature, or
provide information indicating recommended activities for another individual based on the time-based anonymized activity signature.

3. The device of claim 1, wherein the knowledge graph includes:
nodes that represent the activities, and
links representing relations between the activities.

4. The device of claim 1, wherein the one or more processors, when determining the anonymized activity signatures for the individual activities, are to:
utilize the embeddings to calculate activity signatures for the individual activities; and
apply a principal component analysis to the activity signatures to generate the anonymized activity signatures.

5. The device of claim 1, wherein the one or more sensors include one or more of:
a heart rate monitor,
smart glasses,
a fitness tracker,
a smart watch,
smart clothing,
smart jewelry, or
a head mounted display.

6. The device of claim 1, wherein the one or more processors, when utilizing the time-based anonymized activity signature to perform the action, are to:
compare the individual information associated with the individual and information associated with a new individual based on the time-based anonymized activity signature and without divulging the individual information.

7. The device of claim 1, wherein the one or more processors, when determining the anonymized activity signatures for the individual activities, are to:
determine a single anonymized activity signature for each of the individual activities of the individual based on the embeddings.

8. A non-transitory computer-readable medium storing instructions, the instructions comprising:
one or more instructions that, when executed by one or more processors, cause the one or more processors to:
monitor individual activities of an individual over a time period based on sensor information received from one or more sensors associated with the individual;
receive, over the time period, individual information associated with the individual activities of the individual based on monitoring the individual activities;
aggregate and normalize the individual information, based on the time period, to generate normalized aggregated individual information;
identify patterns in the normalized aggregated individual information;
associate states with the patterns based on state information associated with activities capable of being performed by individuals;
generate a sequential knowledge graph based on modifying a knowledge graph with the states and adding a sequence of activities to the knowledge graph;
determine embeddings for the individual activities of the individual based on the sequential knowledge graph;
determine anonymized activity signatures for the individual activities of the individual based on the embeddings,
wherein the one or more instructions, that cause the one or more processors to determine the anonymized activity signatures, cause the one or more processors to:
determine a vector element based on the embeddings,
determine a magnitude parameter of the vector element to create a plurality of intermediate activity signatures, each intermediate activity signature being associated with an activity in a temporal sequence of activities, and
aggregate the plurality of intermediate activity signatures to create an overall anonymized activity signature for the temporal sequence of activities;
generate a time-based anonymized activity signature for the individual based on the anonymized activity signatures; and
utilize the time-based anonymized activity signature to perform an action.

9. The non-transitory computer-readable medium of claim 8, wherein a portion of the individual information is received from the one or more sensors associated with the individual, the one or more sensors including one or more of:
a heart rate monitor, smart glasses,
a fitness tracker,
a smart watch,
smart clothing,
smart jewelry, or
a head mounted display.

10. The non-transitory computer-readable medium of claim 8, wherein the one or more instructions, that cause the one or more processors to generate the sequential knowledge graph, cause the one or more processors to:
combine the states to determine activity types;
modify the activity types with the knowledge graph; and
create the sequence of activities based on modifying the activity types.

11. The non-transitory computer-readable medium of claim 8, wherein the one or more instructions, that cause the one or more processors to determine the embeddings for the individual activities, cause the one or more processors to:
utilize the sequential knowledge graph and a neural network model to determine the embeddings for the individual activities.

12. The non-transitory computer-readable medium of claim 8, wherein the one or more instructions, that cause the one or more processors to determine the anonymized activity signatures for the individual activities, cause the one or more processors to:
utilize the embeddings to calculate activity signatures for the individual activities; and
apply a principal component analysis to the activity signatures to generate the anonymized activity signatures.

13. The non-transitory computer-readable medium of claim 8, wherein the one or more instructions, that cause the one or more processors to generate the time-based anonymized activity signature for the individual, cause the one or more processors to:
concatenate the anonymized activity signatures for the individual activities to generate the time-based anonymized activity signature for the individual.

14. The non-transitory computer-readable medium of claim 8, wherein the one or more instructions, that cause the one or more processors to utilize the time-based anonymized activity signature to perform the action, cause the one or more processors to:
determine a new time-based anonymized activity signature for a new individual; and
compare the individual information and new individual information associated with the new individual based on the time-based anonymized activity signature and the new time-based anonymized activity signature.

15. A method, comprising:
receiving, by one or more processors, and over a time period, individual information associated with individual activities of an individual;
aggregating, by the one or more processors, the individual information, based on the time period, to generate aggregated individual information;
identifying, by the one or more processors, patterns in the aggregated individual information;
determining, by the one or more processors, states for the patterns based on state information associated with activities capable of being performed by individuals;
generating, by the one or more processors, a sequential knowledge graph based on modifying a knowledge graph with the states and adding a sequence of activities to the knowledge graph;
determining, by the one or more processors, embeddings for the individual activities of the individual based on the sequential knowledge graph;
determining, by the one or more processors, anonymized activity signatures for the individual activities of the individual based on the embeddings by:
determining a vector element based on the embeddings,
determining a magnitude parameter of the vector element to create a plurality of intermediate activity signatures, each intermediate activity signature being associated with an activity in a temporal sequence of activities, and
aggregating the plurality of intermediate activity signatures to create an overall anonymized activity signature for the temporal sequence of activities; and
combining, by the one or more processors, the anonymized activity signatures to generate a time-based anonymized activity signature for the individual,
the time-based anonymized activity signature providing information that may be utilized without divulging the individual information.

16. The method of claim 15, further comprising:
utilizing the time-based anonymized activity signature to perform an action.

17. The method of claim 16, wherein utilizing the time-based anonymized activity signature to perform the action comprises:
determining a new time-based anonymized activity signature for a new individual; and
comparing the individual information and new individual information associated with the new individual based on the time-based anonymized activity signature and the new time-based anonymized activity signature.

18. The method of claim 15, wherein determining the anonymized activity signatures comprises:
utilizing the embeddings to calculate activity signatures for the individual activities; and
applying a principal component analysis to the activity signatures to generate the anonymized activity signatures.

19. The method of claim 15, wherein generating the sequential knowledge graph comprises:
combining the states to determine activity types;
modifying the activity types with the knowledge graph; and
creating the sequence of activities based on modifying the activity types.

20. The method of claim 15, wherein determining the anonymized activity signatures for the individual activities comprises:
utilizing the embeddings to calculate activity signatures for the individual activities; and
applying a principal component analysis to the activity signatures to generate the anonymized activity signatures.

* * * * *